United States Patent
Orikasa et al.

(10) Patent No.: US 9,901,423 B2
(45) Date of Patent: Feb. 27, 2018

(54) ORTHODONTIC BRACKET

(75) Inventors: Masaaki Orikasa, Fukushima (JP);
Shingo Katayose, Fukushima (JP);
Kosei Endo, Fukushima (JP)

(73) Assignee: TOMY INCORPORATED, Fukushima (JP)

( * ) Notice: Subject to any disclaimer, the term of this patent is extended or adjusted under 35 U.S.C. 154(b) by 0 days.

(21) Appl. No.: 13/819,797

(22) PCT Filed: Sep. 9, 2011

(86) PCT No.: PCT/JP2011/070639
§ 371 (c)(1),
(2), (4) Date: Feb. 28, 2013

(87) PCT Pub. No.: WO2012/036096
PCT Pub. Date: Mar. 22, 2012

(65) Prior Publication Data
US 2013/0171579 A1    Jul. 4, 2013

(30) Foreign Application Priority Data
Sep. 17, 2010  (JP) .................................. 2010-210121

(51) Int. Cl.
*A61C 3/00*   (2006.01)
*A61C 7/28*   (2006.01)
*A61C 7/02*   (2006.01)

(52) U.S. Cl.
CPC ............... *A61C 7/287* (2013.01); *A61C 7/02* (2013.01); *A61C 7/285* (2013.01)

(58) Field of Classification Search
CPC .... A61C 7/00; A61C 7/12; A61C 7/14; A61C 7/287
(Continued)

(56) References Cited

U.S. PATENT DOCUMENTS 4,144,642 A * 3/1979 Wallshein ............... A61C 7/30
433/11
4,197,642 A * 4/1980 Wallshein ............... A61C 7/30
433/11
(Continued)

FOREIGN PATENT DOCUMENTS

DE    102004056168 B4    9/2007
JP         50-80694 A       6/1975
(Continued)

OTHER PUBLICATIONS

International Search Report (PCT/ISA/210), dated Oct. 18, 2011, issued by the International Searching Authority in counterpart International Patent Application No. PCT/JP2011/070639.
(Continued)

*Primary Examiner* — Matthew Nelson
(74) *Attorney, Agent, or Firm* — Sughrue Mion, PLLC

(57) ABSTRACT

A bracket body 3 is fixed to a base part 2, and a clip 4 is mounted on the bracket body 3 so as to move. An archwire slot 5 is provided on an upper face of the bracket body 3. A guide groove 9 for guiding a lower extended part 42 of the clip 4 is formed on a lower face of the bracket body 3, and provided at a position below the archwire slot 5. In a state where the slot is closed, an end 45 of the lower extended part 42 does not pass through the bracket body 3 up to a side face at an opposite side to a curved part of the bracket body 3. It is possible to provide an orthodontic bracket which has a lower height and has less possibility that a clip may be detached.

10 Claims, 12 Drawing Sheets

(58) Field of Classification Search
USPC .................................................. 433/8–24
See application file for complete search history.

(56) References Cited

U.S. PATENT DOCUMENTS

| | | | | |
|---|---|---|---|---|
| 5,711,666 | A * | 1/1998 | Hanson | A61C 7/145 433/11 |
| 5,906,486 | A * | 5/1999 | Hanson | A61C 7/287 433/10 |
| 5,967,773 | A * | 10/1999 | Roman | A61C 7/30 433/11 |
| 6,071,119 | A * | 6/2000 | Christoff | A61C 7/287 433/13 |
| 6,655,957 | B2 | 12/2003 | Abels et al. | |
| 2002/0110772 | A1 | 8/2002 | Abels et al. | |
| 2002/0110775 | A1* | 8/2002 | Abels | A61C 7/125 433/11 |
| 2002/0110776 | A1 | 8/2002 | Abels et al. | |
| 2002/0119414 | A1* | 8/2002 | Orikasa | A61C 7/287 433/10 |
| 2003/0039938 | A1* | 2/2003 | Orikasa | A61C 7/287 433/11 |
| 2004/0170942 | A1* | 9/2004 | Heiser | A61C 7/28 433/11 |
| 2006/0204918 | A1* | 9/2006 | Voudouris | A61C 7/287 433/11 |
| 2007/0166658 | A1* | 7/2007 | Voudouris | A61C 7/285 433/10 |
| 2007/0269763 | A1* | 11/2007 | Schendell-Groling | A61C 7/287 433/10 |
| 2009/0075227 | A1* | 3/2009 | Opin | A61C 7/287 433/11 |
| 2010/0311004 | A1* | 12/2010 | Voudouris | A61C 7/287 433/11 |

FOREIGN PATENT DOCUMENTS

| | | |
|---|---|---|
| JP | 10-192302 A | 7/1998 |
| JP | 2001-503305 A | 3/2001 |
| JP | 2004-255190 A | 9/2004 |
| JP | 2004-526484 A | 9/2004 |
| JP | 4411573 B2 | 2/2010 |
| JP | 4444410 B2 | 3/2010 |

OTHER PUBLICATIONS

Written Opinion (PCT/ISA/237), dated Oct. 18, 2011, issued by the International Searching Authority in counterpart International Patent Application No. PCT/JP2011/070639.

European Search Report dated Jul. 4, 2014 from the European Patent Office corresponding International Application No. 11825099.2.

Office Action dated May 7, 2015 issued by Japanese Patent Office in counterpart Japanese Patent Application No. 2012-265129.

Notification of Reasons for Refusal dated Nov. 4, 2015 by the Japanese Patent Office in related Application No. 2012-265129.

Advertisement of the opponent on p. 11 of No. 3 of the magazine Kieferorothopadie Nachrichten dated Mar. 2009. TMP1 (1 page total).

Report on the presentation of the QuicKlear brackets on the IDS fair on p. 21 in No. 5 of the magazine Kieferorthopadische Nachrichten dated May 2009. TMP2 (2 pages total).

Invoice dated Aug. 14, 2009 on the purchase of a starter kit and extract from Ifax archive of delivery of starter kit order. TMP3 and TMP3a (2 pages total).

Photograph of front side and rear side of a QuicKlear brackets starter kit from the year 2009. Annex TMP4 (2 pages total).

Photographs of scaled enlarged demonstration model of a QuicKlear bracket. Annex TMP5 (5 pages total).

Notice of Opposition dated Sep. 19, 2016 issued by the European Patent Office in counterpart European Patent Application No. 11825099.2.

* cited by examiner

ORTHODONTIC BRACKET

TECHNICAL FIELD

The present invention relates to an orthodontic bracket which is used for correcting a misaligned tooth or a twisted tooth.

BACKGROUND ART

Conventionally, on occasion of conducting an orthodontic treatment, there has been employed a ligating method in which ligation is performed by inserting an archwire into an archwire slot of an orthodontic bracket which is attached to a tooth of a patient, and by hooking a ligating tool such as a ligature ring formed of resin or a ligature wire formed of stainless steel on tie wings of the orthodontic bracket so that the archwire may not be detached.

On the other hand, an orthodontic bracket requiring no ligating work which is called as "a self-ligating bracket" has been disclosed in Patent Documents 1 and 2. In case where this self-ligating bracket is used for the treatment, a trouble of attaching the ligating tool to the orthodontic bracket is eliminated, and therefore, it is possible for a doctor to reduce a time for applying the treatment to a patient (a chair time). In addition, stick of food residue to the orthodontic bracket and the ligating tool, after the ligating tool has been attached, will not occur, and therefore, it is possible to keep a cavity in a mouth hygienic.

The self-ligating bracket as described above is provided with a clip of a sliding type or a rotary type. By moving this clip, the archwire is held in the archwire slot or detached from the archwire slot.

PRIOR ART DOCUMENT

PATENT DOCUMENT

Patent Document 1: Japanese Patent No. 4444410
Patent Document 2: Japanese Translation of PCT International Application Publication No. JP-T-2001-503305
Patent Document 3: Japanese Patent No. 4411573

SUMMARY OF THE INVENTION

Problems that the Invention is to Solve

An orthodontic bracket 1A in the above described Patent Document 1 is provided with a clip 4A of a sliding type, as shown in FIG. 10. A lower extended part of this clip 4A is formed longer than an upper extended part. For this reason, in case where the clip 4A is inserted at a large angle with respect to a base part 2A of the orthodontic bracket, depending on a curvature of a surface of a tooth to be treated or an angle of the base part (torque), there is such anxiety that an extended end of the lower extended part may interfere with the base part 2A or the tooth, when the clip 4A is inserted up to a slot closing position. For the purpose of preventing this interference, a wall thickness of a bracket body 3A in a part below a slot 5A is formed thick.

The reason for the above will be described in detail herein below.

When an orthodontic treatment employing the orthodontic bracket of a torque-in base type is conducted, it is necessary to directly or indirectly attach a plurality of the orthodontic brackets 1A to the teeth. On this occasion, a curvature of a tooth face and a position where the orthodontic bracket 1A is to be attached are sometimes different between an upper jaw and a lower jaw, and between an anterior tooth and a posterior tooth. As the results, in the orthodontic bracket 1A which has been attached to a specific tooth, an angle provided between a bottom face of the slot 5A and the base part 2A which is fixed along a contour of the tooth face may become large, in some cases.

Under the circumstances, in order to prevent the interference between the base part 2A and the clip 4A, it is considered, for example, to design the orthodontic bracket 1A in such a manner that a sliding direction of the clip 4A is parallel to the bottom face of the slot 5A as shown in FIG. 10. However, in this case, it is necessary to make the thickness of the part below the slot 5A larger than such a thickness that the lower extended part of the clip 4A can pass it through. This is because in case where the thickness of the part below the slot 5A is small, the extended end of the lower extended part of the clip 4A may interfere with the base part 2A, and the clip 4A cannot be slid up to a desired position.

Particularly in the clip 4A of the sliding type, the extended end of the lower extended part is so formed as to pass through the bracket body 3A. Accordingly, the lower extended part is formed longer, and the part of the bracket body 3A below the slot 5A tends to have a larger thickness for the purpose of avoiding the interference. In case where the part below the slot 5A is formed thick as described above, and a total height of the bracket is increased, there is such a problem that a back side of a lip of the patient is likely to touch the orthodontic bracket 1A, and the patient may feel uncomfortable.

On the other hand, the orthodontic brackets disclosed in Patent Documents 2 and 3 adopt clips of a rotary type. An orthodontic bracket 1B disclosed in Patent Document 2 adopts a clip 4B of the rotary type, as shown in FIG. 11. In this orthodontic bracket 1B, the clip 4B is rotated around its lower end 41B, and thus, a slot 5B is opened. A lower extended part of this clip 4B of the rotary type is shorter than that of the aforesaid clip 4A of the sliding type. Accordingly, the bracket body 3B need not have a large wall thickness, and the orthodontic bracket 1B can be made smaller in height.

However, the orthodontic bracket 1B provided with the clip 4B of the rotary type has such a problem that the archwire is likely to be detached. For example, an unexpected strong force is applied to the archwire, in some cases, when the patient bites a hard food, or the archwire is caught by something, during the orthodontic treatment. On this occasion, a force in a direction of withdrawing the archwire from the slot 5B is exerted on the archwire, and the archwire tends to lift the upper extended part of the clip 4B. As the results, there have been such cases that the clip 4B is rotated to open the slot 5B, and the archwire is detached, and that the clip 4B is deformed, and the orthodontic bracket 1B must be exchanged.

An orthodontic bracket 1C disclosed in Patent Document 3 also adopts a clip 4C of the rotary type, as shown in FIG. 12. In this orthodontic bracket 1C, the clip 4C is once slid sideward thereby to displace a lower end 41C of the clip 4C to a rotating part 9C, and thereafter, the clip 4C is rotated around the lower end 41C. In this manner, the slot 5C is opened.

Also in this clip 4C having such a structure, when a force in a direction of withdrawing the archwire from the slot 5C is exerted on the archwire, and a force for lifting the upper extended part of the clip 4C is applied, the clip 4C moves sideward by elastic restoring force of the clip 4C. As the results, there have been such cases that the clip 4C is rotated to open the slot 5C, and the archwire is detached, and that the clip 4C is deformed, and the orthodontic bracket 1C must be exchanged.

Under the circumstances, the invention has been made in view of the above described problems, and an object of the invention is to provide an orthodontic bracket which has a lower height, and has less possibility that a clip may be detached.

Means for Solving the Problems

In order to achieve the object, the invention provides the following bracket:

(1) An orthodontic bracket comprises:

a base part in a plate-like shape which is directly or indirectly fixed to a tooth at its bottom face;

a bracket body which is fixed to an upper face of the base part; and a clip having a substantially U-shape in section which is mounted on the bracket body so as to move, and includes an upper extended part extending along an upper face of the bracket body, a lower extended part extending along a lower face of the bracket body, and a curved part interconnecting the upper and lower extended parts, wherein an archwire slot in a shape of a groove capable of containing an archwire is provided on the upper face of the bracket body so as to extend in a direction perpendicular to a moving direction of the clip, an engaging part into which an end of the upper extended part of the clip can be inserted is provided on a side face at an opposite side to the curved part of the archwire slot, a guide groove for guiding the lower extended part in the moving direction of the clip is provided on the lower face of the bracket body, the guide groove being provided below the archwire slot, and in a state where the end of the upper extended part of the clip is inserted into the engaging part, an end of the lower extended part of the clip does not pass through the bracket body up to an end face at the opposite side to the curved part of the bracket body.

(2) In the orthodontic bracket of (1), the guide groove has a flat face part which is positioned below the archwire slot substantially in parallel with a bottom face of the archwire slot.

(3) In the orthodontic bracket of (1) or (2), a wire retaining hood part which protrudes toward the curved part is provided above the engaging part, and a protruding end of the wire retaining hood part is positioned more remote from the curved part than the side face at the opposite side to the curved part of the archwire slot.

(4) In the orthodontic bracket of any one of (1) to (3), the end of the lower extended part of the clip is provided with an enlarged width part, and the guide groove is provided with a clip retaining part at the curved part side of the guide groove, the clip retaining part having a smaller distance therebetween than a width of the enlarged width part of the clip.

(5) In the orthodontic bracket of any one of (1) to (4), an excessive opening preventing part is provided on the upper extended part of the clip, and an excessive opening preventing projection to be engaged with the excessive opening preventing part is provided on the upper face of the bracket body at the curved part side.

(6) In the orthodontic bracket of any one of (1) to (5), both ends in a lateral direction of the upper extended part of the clip are projected in a bifurcated shape, the engaging part is provided on the archwire slot as engaging parts so as to correspond to the ends of the upper extended part which are projected in the bifurcated shape, a tool guiding face which is in flush with the side face at the opposite side to the curved part of the archwire slot is provided between the engaging parts, and an upper part of the tool guiding face has a taper shape which is open upward.

(7) In the orthodontic bracket of any one of (1) to (5), both ends in a lateral direction of the upper extended part of the clip are projected in a bifurcated shape, and a tool locking projection which projects upward is provided at a center in a lateral direction between the ends of the upper extended part in the bifurcated shape.

(8) In the orthodontic bracket of any one of (1) to (7), a butting wall against which the end of the lower extended part of the clip is butted is provided at the opposite side to the curved part of the guide groove, and the butting wall is provided with a through hole for removing foreign bodies which communicates the guide groove to the exterior.

Advantage of the Invention

According to the orthodontic bracket according to the invention, in a state where the end of the upper extended part of the clip is inserted into the engaging part, the lower extend part of the clip is set to be shorter so that the end of the lower extended part may not pass through the bracket body up to the end face at the opposite side to the curved part. Therefore, in the closed state of the slot where the end of the upper extended part is inserted into the engaging part, the lower extended part of the clip does not interfere with the tooth face, and the thickness of the bracket body can be reduced. As the results, it is possible to reduce the height of the bracket.

Moreover, in case where the archwire tends to lift the upper extended part of the clip, the lower extended part of the clip comes into contact with the guide groove thereby to create a repulsive force against the lifting force. On this occasion, two forces are cancelled by each other, because the guide groove is provided below the archwire slot, and a rotation moment will not be exerted on the clip. Therefore, the clip will not be rotated, and there is no such anxiety that the clip may be opened. As the results, it is possible to provide the orthodontic bracket which has lower height, and has less possibility that the slot may be unintentionally opened.

MODE FOR CARRYING OUT THE INVENTION

Figure 1:
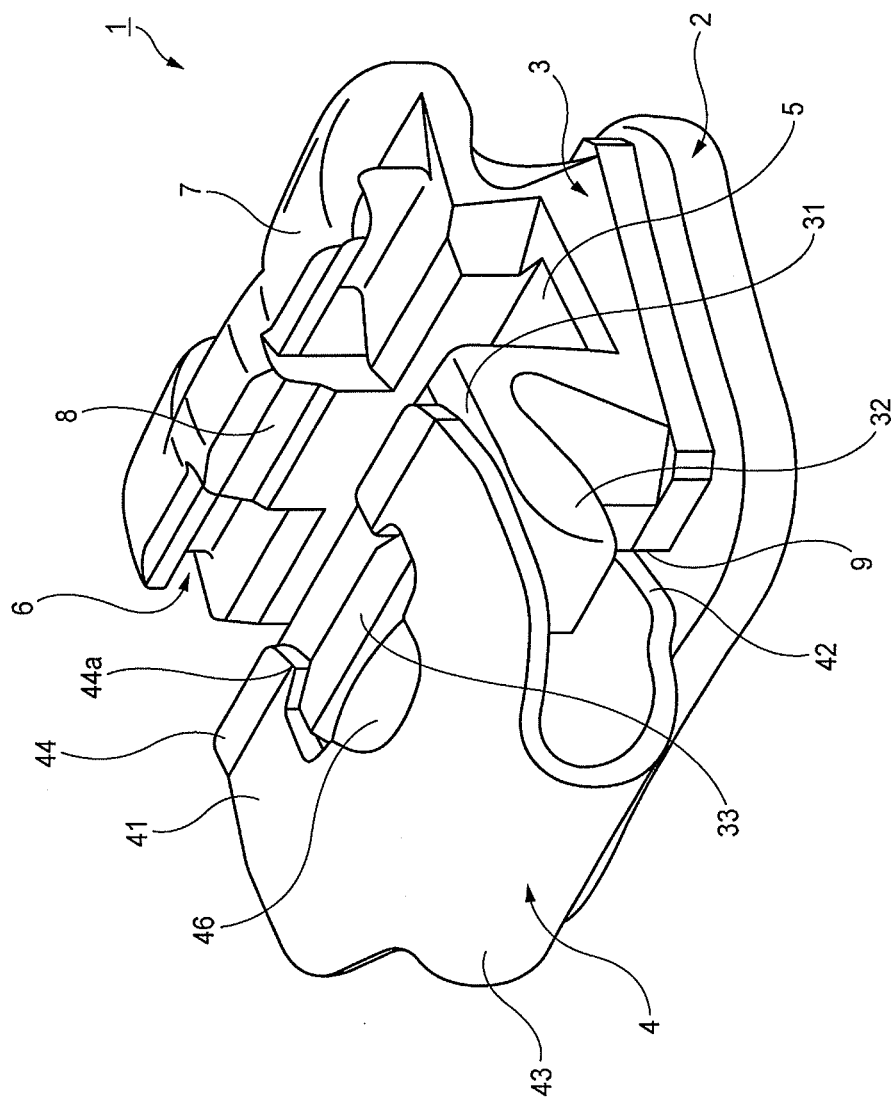
FIG. 1 is a perspective view of an orthodontic bracket according to a first embodiment of the invention.

Now, an orthodontic bracket in an embodiment according to the invention will be described referring to the drawings.
<First Embodiment>

Figure 2:
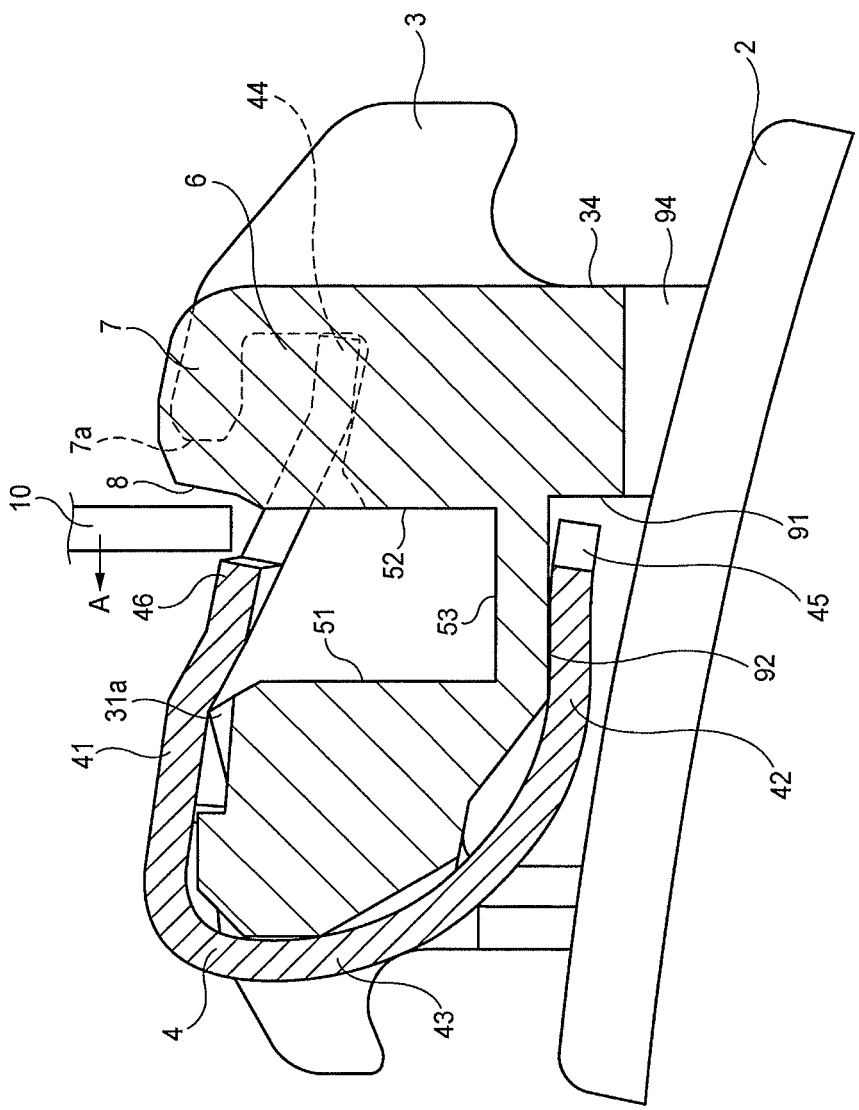
FIG. 2 is a sectional view of the orthodontic bracket as shown in FIG. 1 in a closed state of a slot.
Figure 3:
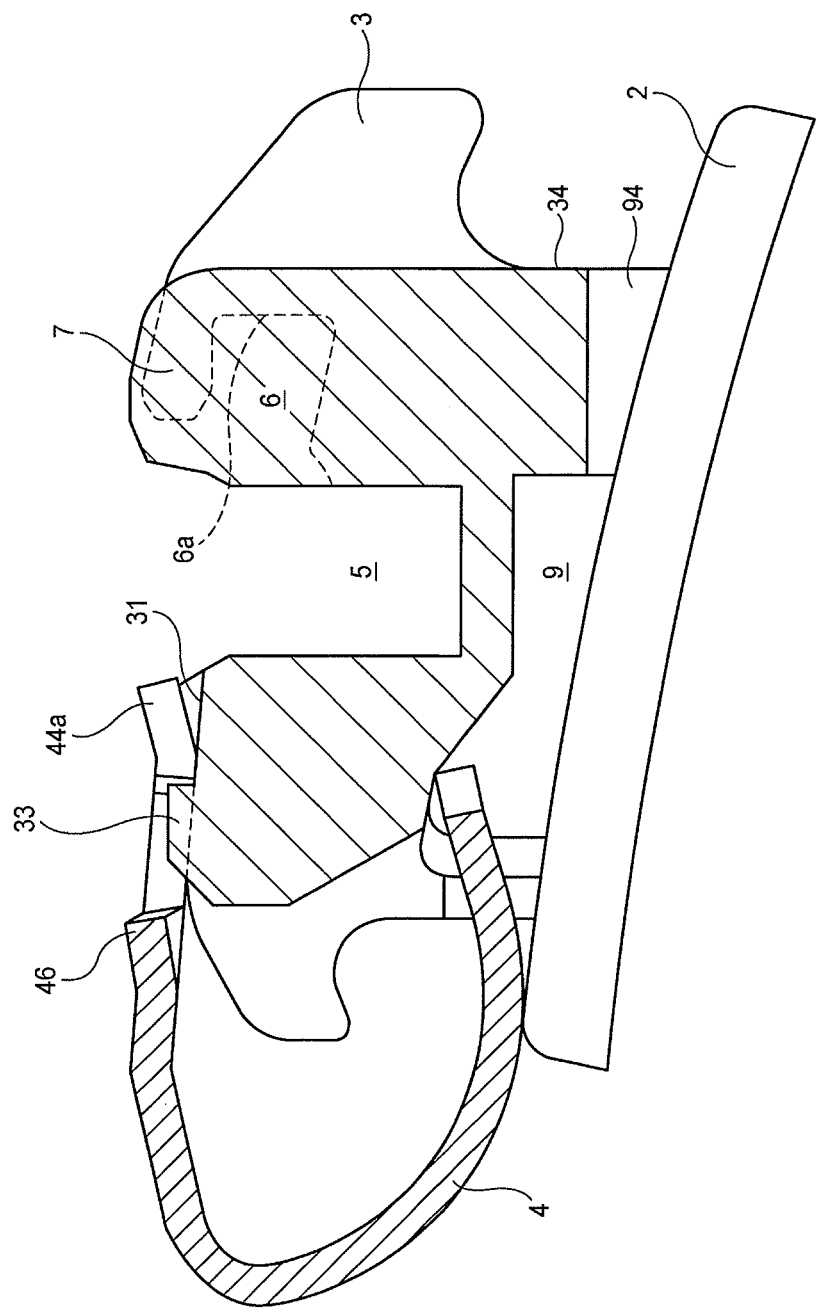
FIG. 3 is a sectional view of the orthodontic bracket as show in FIG. 1 in an opened state of the slot.
Figure 4:
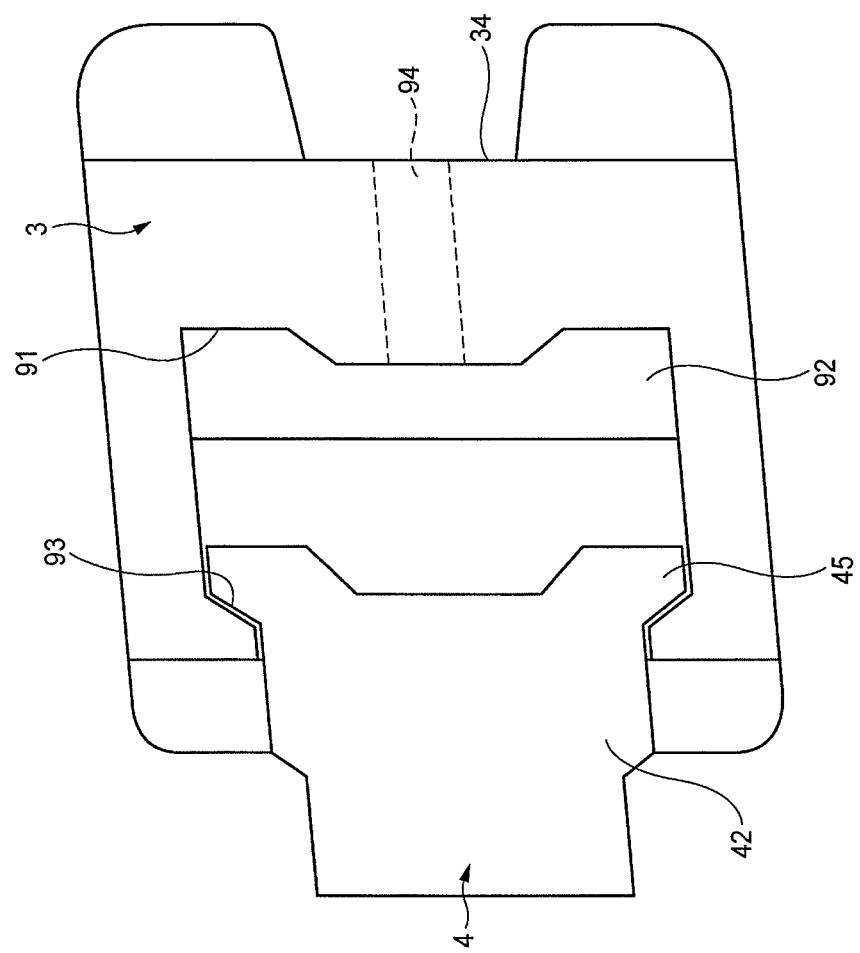
FIG. 4 is a bottom view of a bracket body of the orthodontic bracket as shown in FIG. 1.

An orthodontic bracket 1 in a first embodiment according to the invention will be described referring to FIGS. 1 to 4. FIG. 1 is a perspective view of the orthodontic bracket 1 in the first embodiment, in a state where a slot is opened. FIG. 2 is a sectional view of the orthodontic bracket 1 as shown in FIG. 1, taken along a plane containing an engaging part 6. FIG. 3 is a sectional view of the orthodontic bracket 1, taken along the same plane as in FIG. 2, in a state where the slot is opened. FIG. 4 is a bottom view of a bracket body 3.

As shown in FIG. 1, the orthodontic bracket 1 in the first embodiment according to the invention has a base part 2 in a plate-like shape which can be directly or indirectly fixed to a surface of a tooth at its bottom face, a bracket body 3 which is fixed to an upper face of the base part 2, and a clip 4 which is mounted on the bracket body 3 so as to move. The bracket body 3 in this embodiment is a bracket of a twin type provided with two pairs of wings which are arranged in parallel. It is to be noted that in the following description, a bottom face side of the base part 2 to be fixed to the tooth face is denoted as "a lower side", and a surface side of the base part 2 on which the bracket body 3 is mounted is denoted as "an upper side".

(Bracket Body 3)

As shown in FIGS. 1 and 2, an upper supporting face 31 for supporting an upper extended part 41 of the clip 4 in sliding contact therewith is provided on an upper face of the bracket body 3 (at an opposite side to the base part 2), and a guide groove 9 for guiding a lower extended part 42 of the clip 4 is provided on a lower face of the bracket body 3 (a face close to the base part 2). In this manner, the clip 4 is held on the bracket body 3 so as to move.

Moreover, the bracket body 3 has a pair of right and left protruded parts 32 which are formed at a side close to the clip 4. These protruded parts 32 restrict a position of a curved part 43 of the clip 4, when an archwire slot 5 is closed with the clip 4 (at a slot closing time). Further, a retaining projection (an excessive opening preventing projection) 33 is provided on the upper supporting face 31.

As shown in FIG. 2, the bracket body 3 is provided with an overriding step part 31*a* on the upper supporting face 31 at a side close to the archwire slot 5. This overriding step part 31*a* comes into contact with an upper end 44 of the clip 4, while the archwire slot 5 is not closed with the clip 4 (at a slot opening time). In this manner, the clip 4 is prevented from being unintentionally moved toward the archwire slot 5 thereby to close the archwire slot 5.

(Clip 4)

The clip 4 is an elastically deformable member having a substantially U-shape in section. This clip 4 includes the upper extended part 41 having a planar shape and extending along the upper face of the bracket body 3, the lower extended part 42 having a planar shape and extending along the lower face of the bracket body 3, and the curved part 43 which interconnects these extended parts 41 and 42. A lower end 45 of the lower extended part 42 is extended up to a position below a bottom face 53 of the archwire slot 5.

This clip 4 is curved in such a manner that there is the smallest distance between the upper end 44 and the lower end 45. In this embodiment, the curved part 43 of the clip 4 is so formed as to have a smaller radius of curvature at an upper side to be continued to the upper extended part 41, and a larger radius of curvature at a lower side to be continued to the lower extended part 42. Because the radius of curvature at the upper side is smaller than the radius of curvature at the lower side, the clip 4 will not be prolonged in an upward direction. As the results, a height of the clip 4 is reduced.

Moreover, as shown in FIG. 1, the clip 4 in this embodiment is formed in a bifurcated shape in such a manner that both ends of the upper end 44 in a lateral direction (a longitudinal direction of the archwire slot 5) protrude. Moreover, the upper end 44 of the clip 4 is provided with a tool locking projection 46 which is projected upward, at an intermediate in the lateral direction.

Both tip ends of the bifurcated shape of the upper end 44 of the clip 4 are formed as a pair of right and left inward projections (excessive opening preventing parts) 44*a* which can be engaged with the retaining projection 33 of the bracket body 3. The right and left inward projections 44*a* are so formed as to be smaller in width at their ends. While the slot is opened, the inward projections 44*a* are engaged with the retaining projection 33 of the bracket body 3 thereby to prevent the clip 4 from being opened too much. As the results, an excessive force will not be exerted on the clip 4.

(Archwire Slot 5)

The archwire slot 5 for containing an archwire is formed on the upper face of the bracket body 3 along a direction substantially perpendicular to a moving direction of the clip 4. As shown in FIGS. 2 and 3, this archwire slot 5 is formed as a groove having a substantially U-shape in section which is open upward. This archwire slot 5 includes a side face 51 at a curved part side which is close to the curved part 43 of the clip 4, a side face 52 at an opposite side to the curved part which is opposed to the side face 51 at the curved part side, and the bottom face 53 which interconnects the side face 51 and the side face 52.

A pair of right and left engaging parts 6 are formed on the side face 52 at the opposite side to the curved part of the archwire slot 5. These engaging parts 6 are recessed to an opposite side to the clip 4, so that the bifurcated ends of the upper end 44 of the clip 4 may be inserted therein.

Moreover, hood parts (wire retaining hood parts) 7 are provided above the engaging parts 6 so as to overhang from upper ends of the engaging parts 6 toward the curved part. Even though the archwire tends to lift the upper extended part 41 of the clip 4, while the slot is closed as shown in FIG. 2, the hood parts 7 come into contact with the upper extended part 41 thereby to prevent the clip 4 from being withdrawn from the engaging parts 6.

Overhanging ends 7*a* of the hood parts 7 are positioned more remote from the curved part than the side face 52 at the opposite side to the curved part of the archwire slot 5. This is because in case where the overhanging ends 7*a* are extended up to a position near the side face 52, a wall thickness of the hood parts 7 is inevitably made larger for the purpose of securing rigidity of the hood parts 7 which is required for preventing withdrawal of the clip 4, and accordingly, a total height of the orthodontic bracket 1 is increased.

Moreover, a tool guiding face 8 is formed between a pair of the engaging parts 6, as shown in FIG. 1. The tool guiding face 8 is a face which is formed in flush with the side face 52 at the opposite side to the curved part of the archwire slot 5. When the slot is opened, an opening tool 10 is inserted between this tool guiding face 8 and the tool locking projection 46 of the clip 4, as described below. An upper part of the tool guiding face 8 is formed as a taper face which is open upward. In this manner, a tip end of the opening tool 10 can be easily inserted between the tool locking projection 46 and the tool guiding face 8.

(Guide Groove 9)

The guide groove 9 is formed in a lower part of the bracket body 3. As shown in FIG. 4, the guide groove 9 is formed in a substantially U-shape which is open toward the curved part 43, as seen from a bottom face side. This guide groove 9 is extended along the moving direction of the clip 4, from a position near the curved part 43 of the clip 4 up to a butting wall 91 which is provided at a position below the archwire slot 5.

A width of the guide groove 9 is set to be slightly larger than a width of the lower end 45 of the lower extended part 42 of the clip 4. The lower extended part 42 of the clip 4 is inserted into a space which is formed between this guide groove 9 and the upper face of the base part 2. The lower extended part 42 is guided by the guide groove 9, and hence, the clip 4 is moved.

When the lower extended part 45 of the clip 4 is butted against the butting wall 91 of the guide groove 9, further insertion of the clip 4 is restricted. This butting wall 91 is provided at a position below the side face 52 at the opposite side to the curved part of the archwire slot 5. Accordingly, the lower end 45 of the clip 4 is positioned below the archwire slot 5, while the slot is closed.

Moreover, a flat face part 92 is formed so as to extend from the butting wall 91 of the guide groove 9 toward the curved part 43 of the clip 4. This flat face part 92 is formed substantially in parallel with the bottom face 53 of the archwire slot 5.

In addition, the guide groove 9 is provided, in its end part at the curved part side, with a pair of retaining parts (clip retaining parts) 93 which protrude inward so as to make a distance between them smaller. The lower end 45 of the clip 4 has a larger width than the lower extended part 42. Because the retaining parts 93 hold the lower end 45 of the clip 4, the lower extended part 42 of the clip 4 is prevented from dropping from the guide groove 9. For this purpose, the distance between a pair of the retaining parts 93 is so formed as to be larger than the width of the lower extended part 42 of the clip 4, and as to be smaller than the width of the lower end 45.

Further, a through groove (a through part) 94 for removing a foreign body is provided at the opposite side to the curved part of the guide groove 9 so as to pass through the bracket body 3 up to an end face 34 at the opposite side to the curved part of the bracket body 3. Accordingly, even during the orthodontic treatment where the orthodontic bracket 1 is mounted on a tooth, it is possible to remove the foreign body sticking inside the guide groove 9, by cleaning the guide groove 9 with a water pick or the like from an exterior of the orthodontic bracket 1, by way of the through groove 94. In this manner, a cavity in a mouth can be kept hygienic. Moreover, it is possible to prevent such a trouble that the clip 4 cannot be opened due to the foreign body which has entered between the clip 4 and the guide groove 9.

A width of this through groove 94 is set to be smaller than the width of the lower end 45 of the clip 4, so that the lower end 45 of the clip 4 cannot enter into the through groove 94. As the results, the lower end 45 of the clip 4 will not reach the end face 34 at the opposite side to the curved part of the bracket body 3.

When the orthodontic treatment is conducted, the orthodontic brackets 1 each having the above described structure are respectively attached to a plurality of teeth, and the archwires are inserted into the archwire slots of the respective orthodontic brackets 1. Further, in a state where the archwire slots 5 are closed with the clips 4 to prevent withdrawals of the archwires, an orthodontic force in a direction of correcting dentition is applied to the teeth by way of the orthodontic brackets 1.

(Slot Closing Operation and Slop Opening Operation)

In order to proceed from a closed state of the slot in FIG. 2 to an open state of the slot in FIG. 3, as a first step, the tip end of the opening tool 10 is inserted between the tool locking projection 46 and the tool guiding face 8, as shown in FIG. 2. After the tip end of the opening tool 10 is hooked on the tool locking projection 46, the opening tool 10 is moved together with the clip 4 in a direction of an arrow mark A in FIG. 2, in such a manner that the upper ends 44 of the clip 4 are withdrawn from the hood parts 7.

When the upper ends 44 of the clip 4 are withdrawn from the hood parts 7, the clip 4 is first withdrawn in the lateral direction (to a left side in FIG. 2), while a moving direction of the lower end 45 is restricted within the flat face part 92 of the guide groove 9. Then, the lower end 45 comes into contact with the retaining parts 93, and a lateral movement of the clip 4 is stopped. In a state where the lower end 45 is in contact with the retaining parts 93, the clip 4 is rotated around the lower end 45, as a rotation center. In this manner, the archwire slot 5 is opened.

Because withdrawal of the lower end 45 of the clip 4 is thus prevented by the retaining parts 93, the clip 4 is prevented from dropping from the bracket body 3. Even in case where the archwire slot 5 is opened, for example, for the purpose of exchanging the archwire, after the orthodontic bracket 1 has been attached to the tooth, the clip 4 will not drop from the bracket body 3. Therefore, the orthodontic bracket 1 can be easily treated.

On the contrary to the above, when the slot is closed, the clip 4 is first rotated around the lower end 45 which is in contact with the retaining parts 93, as the rotation center. Thereafter, the clip 4 is slid in the lateral direction along the flat face part 92, thereby allowing the upper ends 44 to be inserted into the engaging parts 6. On this occasion, the upper ends 44 are rotated downward along with the rotation of the clip 4, and in a state where the upper ends 44 are lowered, the clip 4 is laterally moved toward the hood parts 7. Because the hood parts 7 into which the upper ends 44 are inserted can be formed at a lower position, it is possible to reduce the total height of the orthodontic bracket 1.

(Operation)

According to the orthodontic bracket 1 in the above described embodiment, even in the closed state of the slit as shown in FIG. 2, the lower extended part 42 of the clip 4 will not pass through the bracket body 3 up to the end face 34 at the opposite side to the curved part, and the lower end 45 of the clip 4 is positioned below the archwire slot 5. Accordingly, the lower extended part 42 of the clip 4 is shorter, as compared with the orthodontic bracket provided with the clip of the sliding type which is disclosed, for example, in Patent Document 1.

Particularly, as compared with the orthodontic bracket provided with the clip of the sliding type in which the part below the archwire slot is formed thicker as disclosed in Patent Document 1, in the orthodontic bracket 1 according to this embodiment, the thickness of the part below the archwire slot 5 can be made smaller, because the lower extended part 42 is shorter, and will not interfere with the tooth face. As the results, it is possible to reduce the total height of the orthodontic bracket 1. In this manner, the patient equipped with the orthodontic bracket 1 scarcely feels uncomfortable.

During the orthodontic treatment, when a force for withdrawing the archwire from the archwire slot 5 is exerted on the archwire, the archwire applies an upwardly pushing force to the upper extended part 41 of the clip 4. On this occasion, the lower extended part 42 of the clip 4 receives a repulsive force from the guide groove 9. Because the lower extended part 42 of the clip 4 is extended up to the position below the bottom face 53 of the archwire slot 5, the upper extended part 41 and the lower extended part 42 of the clip 4 are subjected to the forces from above and below via the archwire slot 5. Accordingly, the forces to be exerted on the clip 4 are cancelled by each other, and hence, a rotation moment will not be exerted on the clip 4. Therefore, according to the orthodontic bracket 1 in this embodiment, the clip 4 will not be unintentionally rotated, and there is no such anxiety that the archwire slot 5 may happen to be opened.

In the conventional clip of the rotary type as described in Patent Documents 2 and 3, the lower end of the clip is extended only up to a lower part at the curved part side than the archwire slot. For this reason, when a force for withdrawing the archwire from the archwire slot 5 is exerted on the archwire, the forces exerted on the upper extended part and the lower extended part are not cancelled by each other, and there is such anxiety that the archwire may drop from the bracket body.

Moreover, the archwire is guided by the two side faces 51, 52 of the archwire slot 5, and therefore, the force from the archwire is exerted on the upper extended part 41 of the clip 4 perpendicularly to the bottom face 53 of the archwire slot 5. On the other hand, the flat face part 92 of the guide groove 9 is formed substantially in parallel with the bottom face 53 of the archwire slot 5, and therefore, the repulsive force from the flat face part 92 of the guide groove 9 is exerted on the lower extended part 42 of the clip 4 perpendicularly to the bottom face 53 of the archwire slot 5. Therefore, according to the orthodontic bracket 1 in this embodiment, the two forces which are exerted on the clip 4 can be reliably cancelled by each other.

Even though the clip 4 is forced to be moved further, after the archwire slot 5 has been opened by moving the clip 4, the inward projections 44a of the clip 4 are retained by the retaining projection 33 of the bracket body 3. Because further movement and deformation of the clip 4 are thus prevented, a breakdown of the clip 4 can be prevented. Moreover, because the lower extended part 42 of the clip 4 is restrained by the retaining parts 93 of the guide groove 9, the clip 4 will not drop from the orthodontic bracket 1. As the results, it is possible to easily handle the orthodontic bracket.

Although a case where the butting wall 91 of the guide groove 9 is positioned below the bottom face 53 of the archwire slot 5 has been described in the above described embodiment, it is also possible to set the position of the butting wall 91 of the guide groove 9, for example, between a position below the side face 51 of the archwire slot 5 at the curved part side and a position below the side faces 6a at the opposite side to the curved part of the engaging parts 6.

Even in the case where the position of the butting wall 91 is set as described above, the lower end 45 of the clip 4 is restricted by the butting wall 91 of the guide groove 9 in a closed state of the slot, and the lower end 45 of the clip 4 is positioned between the position below the side face 51 of the archwire slot 5 at the curved part side and the position below the side faces at the opposite side to the curved part of the engaging parts. Therefore, the lower end 45 of the clip 4 is restrained from interfering with the tooth face, as described above, and hence, it is possible to reduce the height of the orthodontic bracket 1.

(Second Embodiment)

Figure 5:
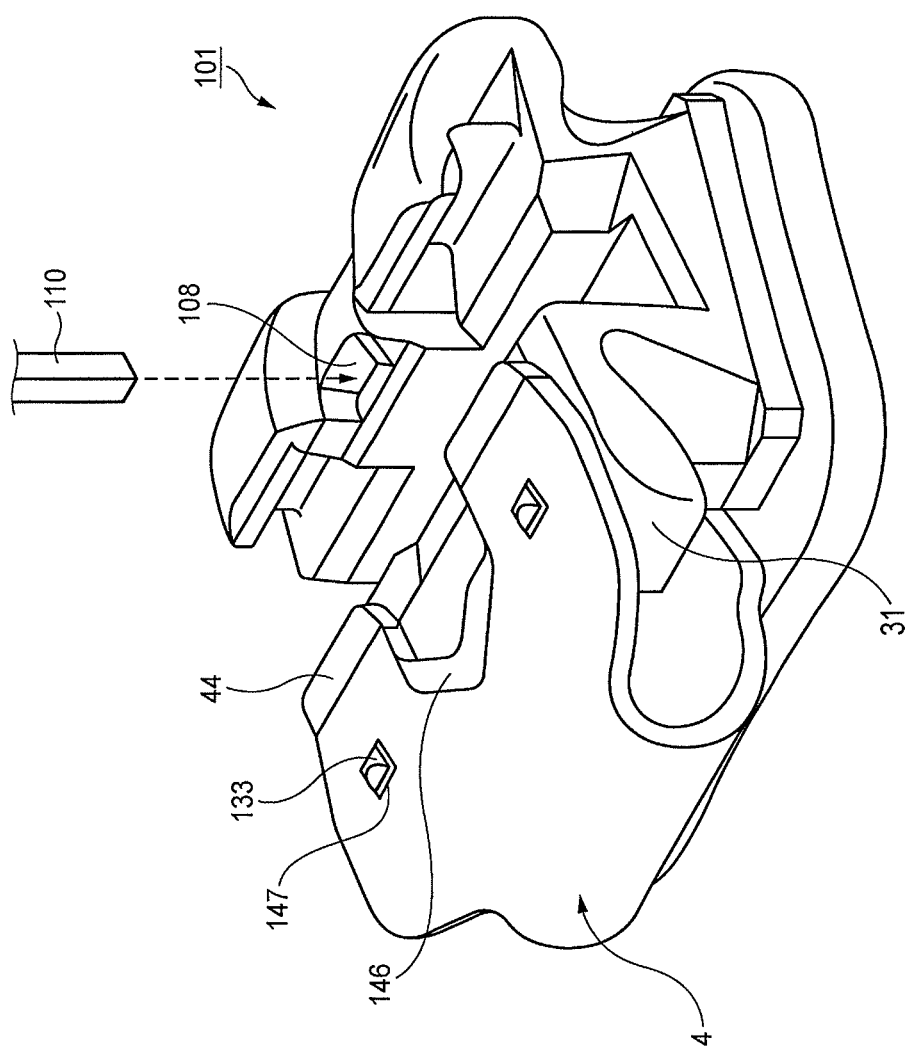
FIG. 5 is a perspective view showing an orthodontic bracket according to a second embodiment of the invention.

In the above described first embodiment, an example in which the clip 4 is moved by the opening tool 10 in a plate-like shape has been described. However, the invention is not limited to this embodiment. FIG. 5 is a perspective view showing an orthodontic bracket 101 in a second embodiment according to the invention. The orthodontic bracket 101 in the second embodiment is different from the orthodontic bracket 1 in the first embodiment only in an engaging structure with a tool and a locking structure for retaining a clip. Therefore, in the following description, only the features which are different from the first embodiment will be described. The same members are denoted with the same reference numerals, and description of the same will be omitted.

There is provided, in the second embodiment, the orthodontic bracket 101 to which an opening tool 110 in a rod-like shape can be applied. A tool guiding face 108 in the second embodiment is formed as a dented part which is slightly larger than the opening tool 110 in the rod-like shape. Moreover, a part between a pair of right and left upper ends 44 of the clip 4 is formed in a V-shape corresponding to a shape of a tip end of the opening tool 110, and a tool locking projection 146 is erected also in a V-shape. Therefore, by inserting the opening tool 110 between the tool guiding face 108 in a dented shape and the tool locking projection 146 in a V-shape, and hooking the opening tool 110 on the tool locking projection 146 thereby to move the clip 4, it is possible to bring the slot into an open state.

In addition, retaining projections 133 are provided on the upper supporting face 31 of the bracket body 3, and a pair of right and left engaging holes 147 in a rectangular shape are formed in the upper extended part 41 of the clip 4. After the clip 4 is moved for the purpose of opening the slot, the retaining projections 133 of the bracket body 3 are engaged with the engaging holes 147 of the clip 4, so that the clip 4 may not be opened too much.

(Third Embodiment)

In the above described first and second embodiments, an example where the upper ends 44 of the clip 4 having a bifurcated shape are inserted into the engaging parts 6 thereby to close the archwire slot 5 has been described. However, the invention is not limited to this structure. An orthodontic bracket 201 in a third embodiment according to the invention will be described, referring to FIGS. 6 and 7.

The orthodontic bracket 201 in the third embodiment is different from the orthodontic bracket 1 in the first embodiment only in that the clip and a part of the bracket body surrounding the engaging part have different shapes. Therefore, in the following description, only the features which are different from the first embodiment will be described. The same members are denoted with the same reference numerals, and description of the same will be omitted.

Figure 6:
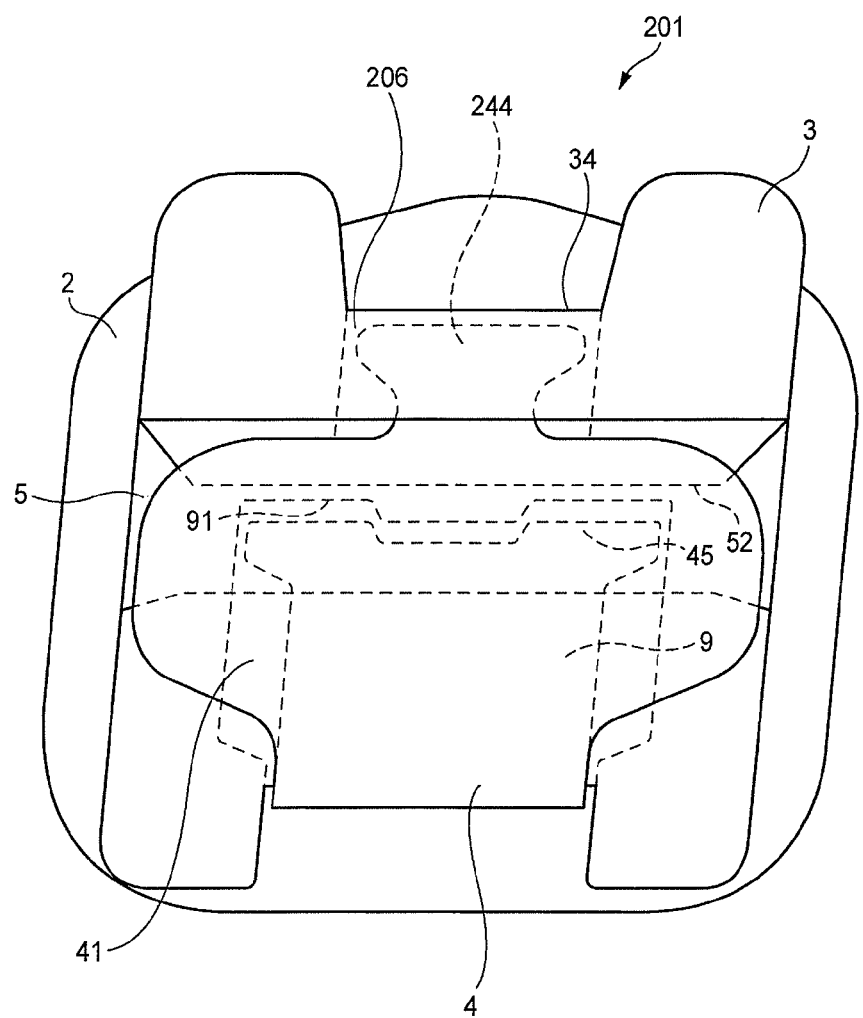
FIG. 6 is a plan view of an orthodontic bracket according to a third embodiment of the invention in a closed state of a slot.
Figure 7:
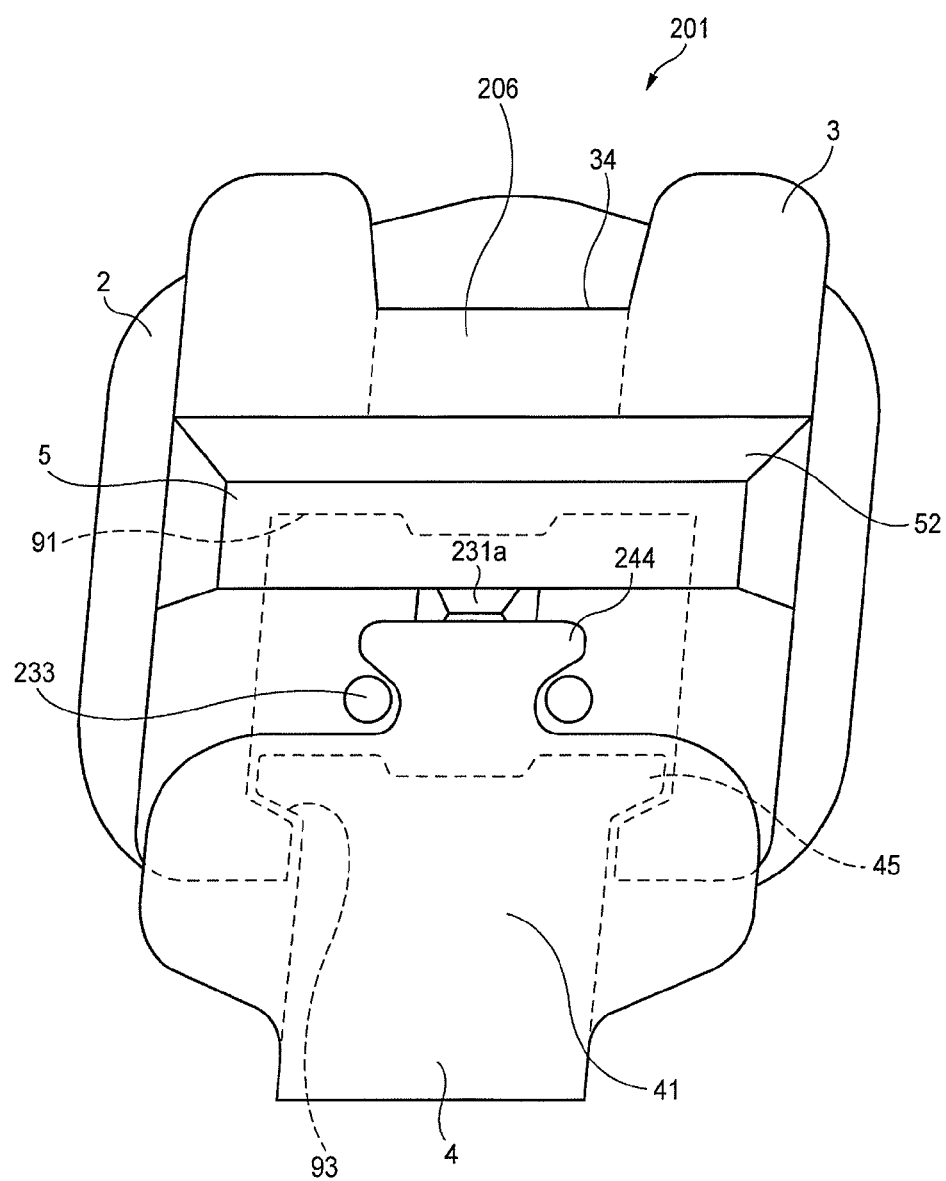
FIG. 7 is a plan view of the orthodontic bracket according to the third embodiment of the invention in an opened state of the slot.

FIG. 6 is a plan view of the orthodontic bracket 201 in a closed state of the slot, and FIG. 7 is a plan view of the orthodontic bracket 201 in an open state of the slot. In this embodiment, the upper extended part 41 of the clip 4 is provided with an upper end 244 which is projected from a center position in a lateral direction thereof. The side face 52 at the opposite side to the curved part of the archwire slot 5 is provided with an insertion hole 206 into which the upper end 244 of the clip 4 can be inserted. This insertion hole 206 is so foamed as to pass through the bracket body 3 from the side face 52 at the opposite side to the curved part of the archwire slot 5 up to the end face 34 at the opposite side to the curved part of the bracket body 3.

In the closed state of the slot, as shown in FIG. 6, the upper end 244 of the clip 4 is inserted into the insertion hole 206. On this occasion, even though an upward force is exerted on the archwire, and the upper extended part 41 of the clip 4 tends to be lifted upward, an upper face of the insertion hole 206 is butted against the upper end 244 of the clip 4 thereby to prevent withdrawal of the clip 4.

As shown in FIG. 7, in the open state of the slot, excessive opening preventing projections 233 which are provided on the upper supporting face 31 of the bracket body 3 intrude into dented parts which are provided at both sides of a connecting part between the upper end 244 and the upper extended part 41 of the clip 4. In this manner, the clip 4 is prevented from moving too much. Moreover, an overriding step 231a is provided on the upper supporting face 31 of the bracket body 3 at its end close to the archwire slot 5. The open state of the slot is maintained, by butting this overriding step 231a against the upper end 244 of the clip 4.

In this embodiment, in the closed state of the slot, the lower end 45 of the clip 4 does not pass through the bracket body 3 up to the end face 34 at the opposite side to the curved part, and the guide groove 9 is positioned below the archwire slot 5, in the same manner as in the above described first and second embodiments. Therefore, in this embodiment, it is possible to provide the orthodontic bracket 201 having a lower height, and having less possibility that the clip may be detached.

Figure 8:
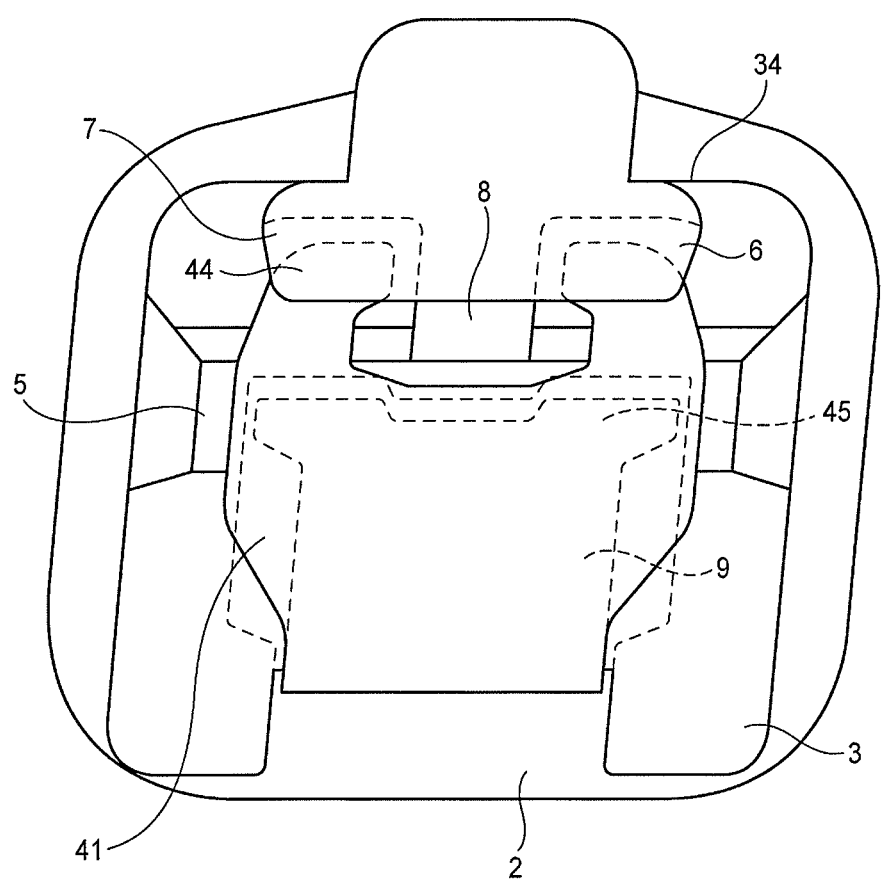
FIG. 8 is a plan view of an orthodontic bracket according to a modification of the invention.

In the above described first to third embodiments, the orthodontic brackets 1, 101, 201 of a twin bracket type having two pairs of the wings which are provided in parallel with the bracket body 3 have been described by way of examples. However, the invention is not limited to the orthodontic bracket of the twin bracket type. FIG. 8 is a plan view of an orthodontic bracket according to a modification of the invention. It is also possible to apply the invention to a single bracket having a single wing, as shown in FIG. 8.

Figure 9:
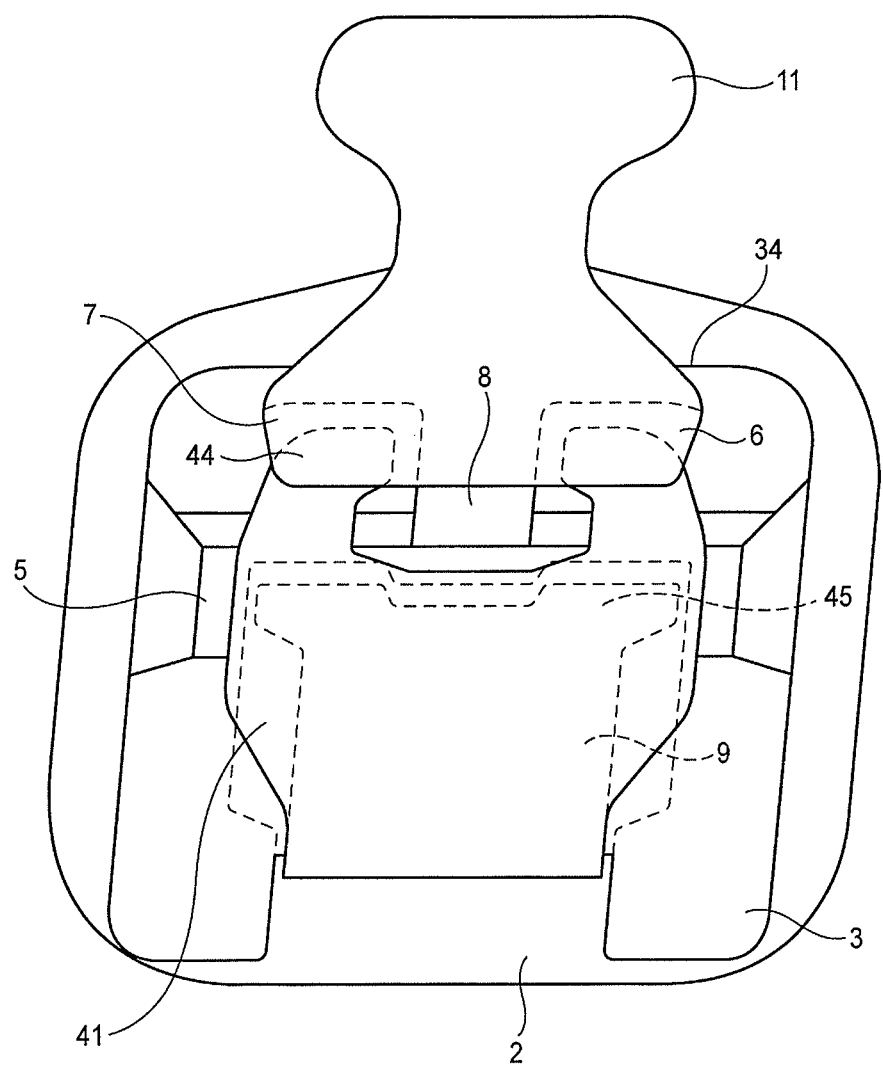
FIG. 9 is a plan view of an orthodontic bracket according to another modification of the invention.
Figure 10:
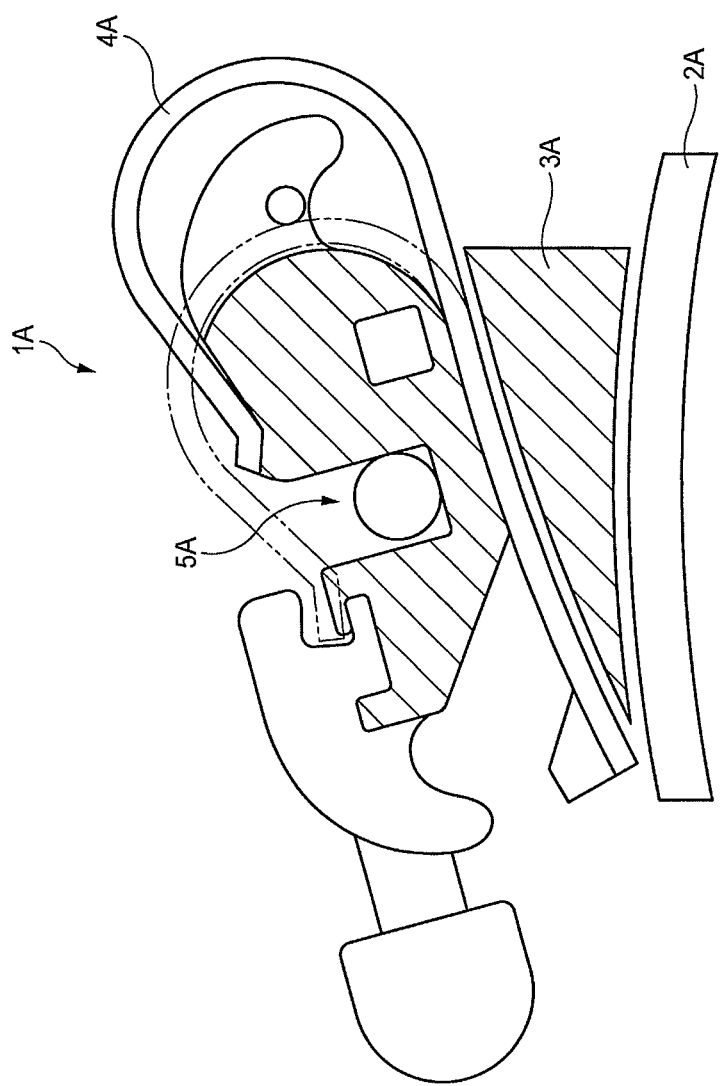
FIG. 10 is a view showing an orthodontic bracket having a clip of a sliding type according to a prior art.
Figure 11:
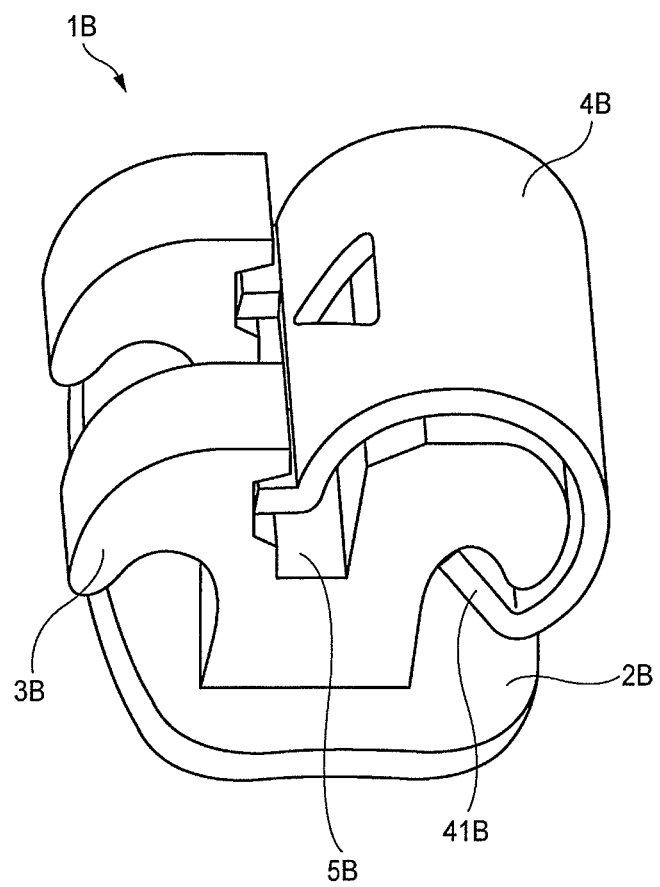
FIG. 11 is a view showing an orthodontic bracket having a clip of a rotary type according to a prior art.
Figure 12:
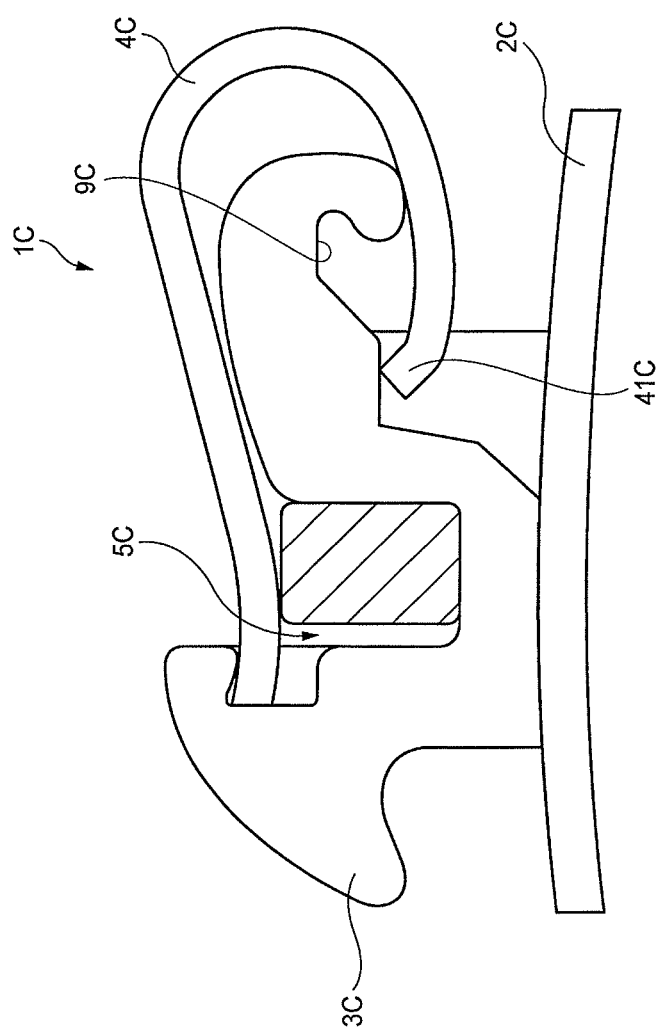
FIG. 12 is a view showing an orthodontic bracket having a clip of a rotary type according to a prior art.

FIG. 9 is also a plan view of an orthodontic bracket according to another modification of the invention which is different from the modification as shown in FIG. 8. As shown in FIG. 9, a hook 11 for hooking an elastic band for drawing may be provided on the bracket body 3. By employing such a structure, it is possible to apply the invention to the orthodontic bracket which can deal with an orthodontic treatment for correcting dentition by hooking the elastic band. Although a case where the orthodontic bracket of the single bracket type is provided with the hook 11 is shown in FIG. 9, as an example, it is also possible to provide the hook 11 on the orthodontic brackets 1, 101, 201 of the twin bracket type in the first to third embodiments.

Also in the modifications as shown in FIGS. 8 and 9, in the closed state of the slot, the lower end 45 of the clip 4 does not pass through the bracket body 3 up to the end face 34 at the opposite side to the curved part, and the guide groove 9 is positioned below the archwire slot 5, in the same manner as in the above described first and second embodiments. Therefore, in these modifications, it is possible to provide the orthodontic bracket 201 having a lower height, and having less possibility that the clip may be detached.

This application is based on Japanese Patent Application (Application No. 2010-210121) filed on Sep. 17, 2010, of which contents are hereby incorporated by reference.

DESCRIPTION OF THE REFERENCE NUMERALS 1, 101, 201 Orthodontic bracket
2 Base part
3 Bracket body
31 Upper supporting face
32 Protruded part
33, 133 Retaining projection (excessive opening preventing projection)
34 End face at an opposite side to a curved part
4 Clip
41 Upper extended part
42 Lower extended part
43 Curved part
44, 244 Upper end
45 Lower end
46, 146 Tool locking projection
147 Engaging hole
5 Archwire slot
51 Side face at a curved part side
52 Side face at an opposite side to a curved part
53 Bottom face
6 Engaging part
206 Insertion hole (Engaging part)
7 Hood part (Wire retaining hood part)
8, 108 Tool guiding face
9 Guide groove
91 Butting wall
92 Flat face part
93 Retaining part
10, 110 Opening tool

The invention claimed is:
1. An orthodontic bracket comprising:
a base part in a plate-like shape which is configured to be attached directly or indirectly to a tooth at a bottom face;
a bracket body which is fixed to an upper face of the base part;
a clip having a substantially U-shaped cross-section which is mounted on the bracket body so as to move, and includes an upper extended part extending along an upper face of the bracket body, a lower extended part extending along a lower face of the bracket body, and a curved part interconnecting the upper and lower extended parts, such that the clip has two ends, a first end of the upper extended part and a second end of the lower extended part, with the curved part interconnecting the upper and lower extended parts;
an archwire slot in a shape of a groove capable of containing an archwire is provided on the upper face of the bracket body so as to extend in a direction perpendicular to a moving direction of the clip;
an engaging part into which the first end of the clip can be inserted is provided on a side face of the archwire slot at an opposite side to the curved part;
a guide groove for guiding the lower extended part in the moving direction of the clip is provided on the lower face of the bracket body, the guide groove being provided under the archwire slot, wherein, in a state where the first end of the clip is inserted into the engaging part, the lower extended part is positioned below a bottom face of the archwire slot, and the second end of the clip does not pass through an end face of the bracket body, the end face being at the opposite side of the curved part, and wherein the lower extended part of the clip does not extend past the archwire slot in a locked position, the locked position being a state in which the first end of the upper extended part is received into the engaging part, wherein the guide groove is provided underneath the archwire slot such that the guide groove is positioned on a hypothetical line drawn perpendicular to a bottom portion of the archwire slot and passing through the bottom portion of the archwire slot, and a tool guiding face is provided at a center of the engaging part in a longitudinal direction of the engaging part, and a space for receiving a tool for opening the clip is provided adjacent to the tool guiding face.

2. The orthodontic bracket as claimed in claim 1, wherein the guide groove has a flat face part which is positioned below the archwire slot substantially in parallel with a bottom face of the archwire slot.

3. The orthodontic bracket as claimed in claim 1, wherein a wire retaining hood part which protrudes toward the curved part is provided above the engaging part, and a protruding end of the wire retaining hood part is positioned more remote from the curved part than the side face of the archwire slot at the opposite side to the curved part.

4. The orthodontic bracket as claimed in claim 1, wherein an excessive opening preventing part is provided on the upper extended part of the clip, and an excessive opening preventing projection to be engaged with the excessive opening preventing part is provided on the upper face of the bracket body at a side of the curved part.

5. The orthodontic bracket as claimed in claim 1, wherein both ends in a lateral direction of the upper extended part of the clip are projected in a bifurcated shape, the engaging part is provided on the archwire slot as engaging parts so as to correspond to the ends of the upper extended part which are projected in the bifurcated shape, a tool guiding face which is in flush with the side face of the archwire slot at the opposite side to the curved part is provided between the engaging parts, and an upper part of the tool guiding face has a taper shape which is open upward.

6. The orthodontic bracket as claimed in claim 1, wherein both ends in a lateral direction of the upper extended part of the clip are projected in a bifurcated shape, and a tool locking projection which projects upward is provided at a center in a lateral direction between the ends of the upper extended part in the bifurcated shape.

7. The orthodontic bracket as claimed in claim 1, wherein the bracket body includes a butting wall which extends below a bottom surface of the archwire slot which defines one end of the guide groove; the lower extended part of the clip abuts against the butting wall in the state where the first end of the clip is inserted into the engaging part, and the butting wall is provided with a through hole for removing foreign bodies which communicates the guide groove to the exterior.

8. The orthodontic bracket as claimed in claim 1, wherein a butting wall which restricts further insertion of the clip when the second end of the clip is butted against the butting wall is positioned below a bottom face of the archwire slot.

9. The orthodontic bracket as claimed in claim 1, wherein a butting wall which restricts further insertion of the clip when the second end of the clip is butted against the butting wall is positioned below a side face of the archwire slot at a side of the curved part.

10. The orthodontic bracket as claimed in claim 1, wherein the second end of the clip is provided with an enlarged width part, and the guide groove is provided, at a side of the curved part, with a pair of clip retaining parts that protrude inward from sides of the guide groove such that a distance between the clip retaining parts is smaller than a width of the enlarged width part of the clip.

* * * * *